United States Patent [19]

Silvestrini et al.

[11] 4,402,956
[45] Sep. 6, 1983

[54] 2-[3-[4-(3-CHLORO-4-FLUOROPHENYL)-1-PIPERAZINYL]PROPYL]-1,2,4-TRIAZOLO[4,3-A]PYRIDIN-3(2H)-ONE

[75] Inventors: Bruno Silvestrini; Leandro Baiocchi, both of Rome, Italy

[73] Assignee: Aziende Chimiche Riunite Angelini Francesco ACRAF SpA, Rome, Italy

[21] Appl. No.: 234,065

[22] Filed: Feb. 12, 1981

[30] Foreign Application Priority Data

Apr. 9, 1980 [IT] Italy ................................ 21246 A/80

[51] Int. Cl.³ .................. C07D 403/00; A61K 31/495
[52] U.S. Cl. .................................... 424/250; 544/366; 546/271
[58] Field of Search ......................... 544/366; 424/250

[56] References Cited

U.S. PATENT DOCUMENTS

T100,505  4/1981  Morrow et al. ..................... 544/366
3,381,009  4/1968  Palazzo et al. ..................... 544/366
4,267,179  5/1981  Heeres et al. ....................... 544/366

OTHER PUBLICATIONS

Diep, B. K. et al., Journal Chem. Society, 2784–2787 (1963).
Burger, A., "Medicinal Chemistry" 1960, p. 43.

*Primary Examiner*—Donald G. Daus
*Assistant Examiner*—S. A. Gibson
*Attorney, Agent, or Firm*—Ladas & Parry

[57] ABSTRACT

Novel compounds selected from the group consisting of 2-[3-[4-(3-chloro-4-fluorophenyl)-1-piperazinyl]-propyl]-1,2,4-triazolo[4,3-a]pyridine-3(2H)-one (I) and from its non-toxic pharmaceutically acceptable salts possess analgesic, anti-convulsant and anti-depressant activities.

2 Claims, No Drawings

2-[3-[4-(3-CHLORO-4-FLUOROPHENYL)-1-PIPERAZINYL]PROPYL]-1,2,4-TRIAZOLO[4,3-A]PYRIDIN-3(2H)-ONE

The invention provides novel compounds selected from the group consisting of 2-[3-[4-(3-chloro-4-fluorophenyl)-1-piperazinyl]propyl]-1,2,4-triazolo[4,3-a]pyridin-3(2H)-one (I) and its non-toxic and pharmaceutically acceptable salts.

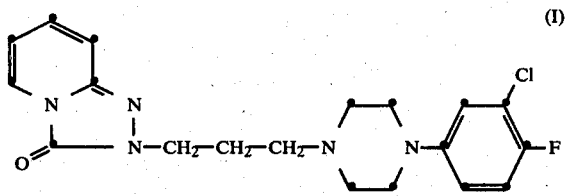

The compounds of the invention were examined in experimental animals using tests which are currently used to show their peculiar activities and were found to posses anti-convulsant and anti-depressant activities.

Compound (I) may conveniently be prepared by reacting 3-chloro-4-fluoro-aniline (II) with compound (III) or with its hydrochloride in suitable solvent, at the boiling point of this latter, according to the following scheme

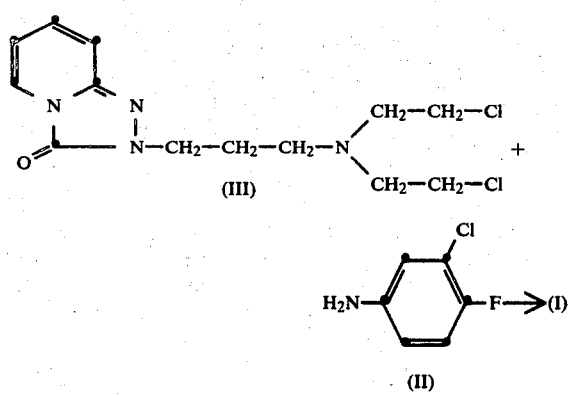

The most suitable solvents for this reaction proved to be those having a boiling point over 100° C. and capable of dissolving the two reagents, namely aliphatic primary alcohols having 4, 5 or 6 carbon atoms.

It was found particularly convenient to perform the reaction in the presence of HCl acceptors such as alkaline carbonates or organic bases. The organic base to be used as an acceptor is preferably a tertiary one (triethylamine, dimethylaniline) or may be an excess of the same 3-chloro-4-fluoroaniline (II). In this latter case at least 3 moles of (II) must be used for one mole of (III) being employed as a free base, whereas when (III)-hydrochloride is used 4 moles of (II) are found necessary.

(I) is separated from the reaction mixture using the usual techniques. The base (I) thus obtained formed into a salt by known methods by mixing the solutions of the base and of the chosen acid in an organic solvent. The pharmaceutically acceptable acids to form the salts are the usual acids. Examples are hydrochloric, sulfuric, nitric, fosforic, pamoic, citric, tartaric, methanesulfonic acid etc.

The compounds posses analgesic, tranquilizing and anti-convulsant effects and are useful for the treatment of pain, depression and convulsions. In the analgesic and tranquilizing effects the compounds are as active as Trazodone, but their action is at least 3 times longer. The anti-convulsant activity is a peculiar feature of the compounds. In fact, Trazodone and other piperazine derivatives have been found to be devoid of this property.

The compounds of the invention have been examined in laboratory animals using tests which are currently used to characterize psychotropic and anti-convulsant agents. These tests are recognized in the art as showing human activity as well. The following tests were used:

(a) Analgesic activity

This was determined by the methods of L. C. Hendershot and J. Forsaith (Antagonism of the frequency of phenylquinone induced writhing in the mouse by weak analgesics and non-analgesics, J. Pharmacol. Exp. Ther. 125, 237–240, 1959) and G. Woolfe and A. A. McDonald (Evaluation of the analgesic action of pethidine hydrochloride (demerol), J. Pharmacol. Exp. Ther. 80, 300–307, 1944). The compounds are active in both these tests at the dose of 4 and 10 mg/kg p.o., respectively.

(b) Tranquilizing activity

This has been studied by the method of S. Irwin (Drug screening and evaluation of new compounds in animals, in: Animal and clinical pharmacologic techniques in drug evaluation, eds.: J. H. Nodine and P. E. Siegler, Year Book Medical Publishers Inc., Chicago, pp. 36–54, 1964) in mice and rats. At the dose of 1 mg/kg p.o. the compounds produce sedation and reduce motor activity and the reaction to stimula. With increasing doses these effects become more marked and at doses above 100 mg/kg p.o. prostration is observed. In these experiments miosis and palpebral ptosis have also been observed indicating a block of the adrenergic system. Effects on the avoidance conditioned response have been studied by using the method of D. Bovet, P. Leathwood, J. Mauron, A. Oliveiro and M. Satta (The effects of different amino acid diet on fast induced performance decrement in mice, Psychopharmacologia 22, 91–99, 1971). At the dose of 10 mg/kg p.o. the compounds inhibit the conditioned avoidance response in mice. The unconditioned avoidance response produced by electric shock is not affected by the compounds up to the dose of 100 mg/kg p.o. In this connection it should be noted that the ability to inhibit specifically the conditioned response is a distinctive feature of Trazodone and neuroleptics; on the contrary, minor tranquilizers or anxiolytics inhibit non-specifically both the conditioned and unconditioned response. To test the anti-dopaminergic activity the apomorphine test in rats has been used (I. Creese and S. D. Iversen, Behavioural sequelae of dopaminergic degeneration: postsynaptic supersensitivity? In: Pre- and postsynaptic receptors. Proceedings of a study-group held at 13th annual meeting of the American College of Neuropsychopharmacology, San Juan, Puerto Rico, eds. E. Usdin, W. E. Burney jr. and M. Dekker, N.Y., vol. 3, pp. 171–187, 1975). The compounds are inactive up to the dose of 25 mg/kg i.p. Trazodone is also inactive, whereas neuroleptics are active; for instance, the active dose of chlorpromazine and haloperidol are 3 and 0.01 mg/kg i.p., respectively.

(c) Anti-convulsant activity

This was determined in mice by using the electroshock (E. A. Swinyard, Laboratory assay of clinically effective anti-epileptic drugs, JAMA 38, 201–204, 1949) and pentylenetetrazole (120 mg/kg s.c.) or strychnine (2,5 mg/kg s.c.). The procedure used was as follows. After administration of the drugs (30 min) to the mice, tonic extensor seizures were produced using sixty Hz shocks of 250 mSec duration and of controlled current strengths delivered through ocular electrodes. At least four groups of 10 mice each (in which convulsions occurred in from 10 to 90% of the animals per group), were used to establish the current strengths required to produce seizures in 50% of the mice ($CS_{50}$). The $CS_{50}$ was estimated from probit logamperage regression lines obtained using probit analysis. For pentylenetetrazole and strychnine was used a procedure similar to that described for electroshock. The compounds inhibit convulsions produced by pentylenetetrazole, whereas they are inactive against convulsions produced by strychnine. The compounds increase the threshold of the electroshock at the dose of 10 mg/kg i.p. Here again the compounds are different from minor tranquilizers which inhibit non-specifically any type of convulsions. This profile of anti-convulsant effects indicates a clinical usefulness for the treatment of petit mal and for the prevention of epileptic attacks rather than for the treatment of grand mal seizures. The results of the tests described above are summarized in the following table.

|  | Compounds | Trazodone |
|---|---|---|
| Tranquilizing activity | + | + |
| Adrenergic blockade | + | + |
| Analgesic activity | + | + |
| Inhibition of 1-dopa response | − | − |
| Selective inhibition of conditioned response | + | + |
| Anti-convulsant activity | + | − |

Except for the anti-convulsant activity, the compounds possess a pharmacological profile very similar to that of Trazodone. The extensive clinical experience accumulated on Trazodone has shown that these pharmacological actions correspond to a therapeutic action, particularly in anxiety and depressive conditions; a detailed discusion of the theoretical and clinical background supporting this conclusion may be found in a recent publication by S. Gershon, K. Rickels and B. Silvestrini (Trazodone—a new approach to the therapy of depressive illness. Round table discussion on Trazodone, a new broadspectrum anti-depressant, 11th C.I.N.P. Congr. Coll. Int. Neuropsychopharmacol., Vienna, Austria, 1978, Excerpta Med. Amsterdam, 1980).

Therefore the compounds too are of therapeutic interest in anxiety and depressive states, with the advantage over Trazodone of a longer duration of action. Besides the duration of action, a distinctive feature of the compounds in respect to Trazodone is the anti-convulsant activity.

The compounds of the invention may be administered orally or parenterally.

In use, the compounds of the invention are administered in conventional formulations, using either the free base or a non-toxic salt of the same with a pharmaceutically acceptable acid, namely in association with pharmaceutical excipients generally used for the production of compositions for oral or parenteral administration.

The optimum dosage rate varies with the severity of the disease. For oral administration the dosage rate is preferably 25–600 mg per subject per day; and for parenteral administration the dosage rate is preferably 10–400 mg per subject per day, taking care to administer the drug in the case of using the high doses by two intravenous infusions per day.

Conventional pharmaceutical compositions for oral administration may be used such as tablets, capsules, and aqueous solutions. The unit dose for both tablet and capsule of active ingredient may be comprised between 25 and 100 mg; the liquid composition may preferably contain 1% by weight of the active ingredient.

The carriers used in the preparation of these compositions are the excipients known in the pharmacist art. In the preparation of tablets, typical excipients include disintegrating agents, e.g. maize starch and lubricant agents, e.g. magnesium stearate; in the preparation of capsules, standard gelatin capsules may be used containing the active ingredient along or admixed with a diluent. The liquid compositions may comprise as excipients water and glycerol.

Conventional pharmaceutical compositions for parenteral administration may be used, for example, a sterile solution in aqueous medium, or a sterile suspension in aqueous or oily media; the unit dose for an ampul of the active ingredient may be between 2.5 and 50 mg; for this purpose preferably a 0.25 to 1% solution may be used.

EXAMPLE I 6.7 g (0.021 mol) Of 2-[3-[bis(2-chloroethyl) amino]-propyl]-1,2,4-triazolo[4,3-a]pyridin-3(2H)-one (III) (L. Baiocchi and M. Giannangeli, Boll. Chim. Farm. 113, 152 (1974) and 9.17 g (0.063 mole) of 3-chloro-4-fluoroaniline (II) (J. Chem. Soc. 1963, 2784) were dissolved in 50 mol of n-amyl alcohol and the solution was refluxed for 90 minutes. Then 20 ml of 50% potassium carbonate solution were added and the mixture was steam-distilled.

After removal of the excess amyl alcohol and 3-chloro-4-fluoroaniline the residue was cooled and 2-[3-[4-(3-chloro-4-fluorophenyl)-1-piperazinyl]propyl]-1,2,4-triazolo[4,3-a]pyridin-3(2H)-one base (I) was separated (5 g. yield 60.7%, m.p. 104°–106°).

NMR spectrum in $CDCl_3$ (TMS as an internal standard): 2.05δ(q, J=6 cps, 2H); 2.55δ(m,6H); 3.00δ(m, 4H); 4.08δ (t, J=6 cps, 2H); 6.30–7.25δ(three multiplets, 6H); 7.75δ (d, J=7 cps, 1H).

Hydrochloride: m.p.=244°–46° (from absolute ethanol).

IR Spectrum $(KBr)_{C=O}=1700$ $cm^{-1}$.

EXAMPLE II

A mixture of 90 gr (0.28 mol) of 2-[3-bis(2-chloro ethyl)amino]propyl]-1,2,4,-triazolo[4,3-a]pyridin-3(2H)-one (III),62 gr of 3-chloro-4-fluoroaniline (0.42 mol) (II),80 ml of triethylamine and 500 ml of n-amyl alcohol was refluxed for 2 hours. After cooling 2N NaOH(150 ml) was added to the mixture and then it was steam-distilled.

The residue was taken up with ethyl acetate and the organic solution was dried on anhydrous sodium sulfate. The hydrochloride was obtained from this dried solution by adding a suitable amount of anhydrous HCl in absolute ethanol solution; the precipitate was collected and recrystallised from absolute ethanol: the yield is 42 gr (35.2%)—m.p.=244°–45°.

The following salts were also prepared using the usual techniques:

| | |
|---|---|
| PHOSPHATE | m.p. = 203.5–205° |
| SULFATE | m.p. = 172.5–174° |
| BENZENESULFONATE | m.p. = 142–145° |
| MALEATE | m.p. = 144–145° |
| MESILATE | m.p. = 101–102° |
| SALICYLATE | m.p. = 132–133° |

We claim:
1. 2-[3-[4-(3-Chloro-4-fluorophenyl)-1-piperazinyl]-propyl]-1,2,4-triazolo[4,3-a]pyridin-3(2H)-one and its non-toxic pharmaceutically acceptable salts.
2. An anti-convulsant psychotropic, analgesic composition comprising an anti-convulsant psychotropic, analgesic amount of the compound according to claim 1, together with a pharmaceutically acceptable carrier.

* * * * *